United States Patent
Chapoy et al.

(10) Patent No.: US 6,942,695 B1
(45) Date of Patent: Sep. 13, 2005

(54) BIOMEDICAL DEVICES WITH POLYIMIDE COATING

(75) Inventors: L. Lawrence Chapoy, Barrington, IL (US); Hermann Faubl, Lake Bluff, IL (US)

(73) Assignee: Wessley-Jessen Corporation, Des Plaines, IL (US)

( * ) Notice: Subject to any disclaimer, the term of this patent is extended or adjusted under 35 U.S.C. 154(b) by 0 days.

(21) Appl. No.: 09/286,530

(22) Filed: Apr. 5, 1999

(51) Int. Cl.[7] ............................................. A61F 2/16
(52) U.S. Cl. .................. 623/6.5; 623/6.62; 623/926
(58) Field of Search .......................... 623/1.46, 6.44, 623/6.5, 6.6, 6.62, 926, 11.11, 23.76

(56) References Cited

U.S. PATENT DOCUMENTS

| | | | |
|---|---|---|---|
| 4,135,887 A | * | 1/1979 | Rossi .......................... 44/331 |
| 4,402,579 A | | 9/1983 | Poler |
| 4,576,607 A | * | 3/1986 | Kelman ........................ 623/6 |
| 4,718,905 A | | 1/1988 | Freeman |
| 4,737,322 A | | 4/1988 | Bruns et al. |
| 4,744,647 A | * | 5/1988 | Meshel et al. .............. 351/177 |
| 5,047,051 A | | 9/1991 | Cumming |
| 5,074,942 A | * | 12/1991 | Kearns et al. .............. 156/154 |
| 5,108,819 A | * | 4/1992 | Heller et al. ................. 428/195 |
| 5,147,397 A | | 9/1992 | Christ et al. |
| 5,241,040 A | | 8/1993 | Cuomo et al. |
| 5,252,262 A | | 10/1993 | Patel |
| 5,266,074 A | | 11/1993 | Nishi et al. |
| 5,326,505 A | | 7/1994 | Adams et al. |
| 5,397,511 A | | 3/1995 | Ishihara et al. |
| 5,415,938 A | | 5/1995 | Cahalan et al. |
| 5,504,830 A | | 4/1996 | Ngo et al. |
| 5,527,415 A | | 6/1996 | Doyle et al. |
| 5,712,327 A | * | 1/1998 | Chang et al. ............... 523/107 |
| 5,919,227 A | * | 7/1999 | Bello ........................ 623/6.64 |
| 6,033,582 A | * | 3/2000 | Lee et al. ..................... 216/37 |
| 6,158,862 A | * | 12/2000 | Patel et al. ................. 351/164 |

* cited by examiner

Primary Examiner—Paul B. Prebilic
(74) Attorney, Agent, or Firm—Gardner Groff, P.C.

(57) ABSTRACT

Intraocular lenses and methods producing the same are provided. The intraocular lens includes an optic and a haptic that are integrally formed together. The haptic has a polyimide coating. The polyimide coating promotes fibrosis in the surrounding eye tissue to enhance the anchoring of the IOL after it is implanted in an eye.

36 Claims, 2 Drawing Sheets

BIOMEDICAL DEVICES WITH POLYIMIDE COATING

BACKGROUND OF THE INVENTION

This invention relates to implantable biomedical devices, such as intraocular lenses (IOLs), and to methods for producing such devices. More particularly, in one aspect, the present invention relates to relatively straightforward and easy to practice methods for producing IOLs, and to such IOLs wherein the optics and haptics are integrally formed of the same material.

The use of IOLs to improve vision and/or to replace damaged or diseased natural lenses in human eyes, particularly natural lenses impaired by cataracts, has achieved wide acceptance. Accordingly, a variety of IOLs have been developed for surgical implantation in the posterior or interior chambers of the eye according to a patient's needs.

Known IOLs comprise an optical lens portion, or optic for short, which includes an optical zone, and one or more, preferably two, supporting structures called fixation members, or haptics for short, for contacting eye tissue to fix or hold the IOL in the proper position after implantation into the eye. The optic may comprise a soft, resilient material, such as a silicone polymeric material or a relatively hard or rigid material such as, for example, polymethylmethacrylate (PMMA). The haptics typically comprise a filament constructed of a resilient metal or polymeric substance, such as PMMA, polyimide or polypropylene.

Each of the filament haptics is preferably flexible to reduce trauma to sensitive eye structures and to be yielding during insertion of the IOL. In addition filament haptics generally have a memory retaining capability, e.g., springiness, so that after implantation of an association IOL, the filament haptic automatically tend to return to their normal orientation.

As an alternative to filament haptics, some IOLs are provided with footplate-type haptics. These footplates generally extend radially outwardly from the optic in the plane of the optic, and terminate in rounded or blunted end configured for placement in an eye chamber. The material for such footplates have included soft materials, for example silicone or 2-hydroxyethyl methacrylate (HEMA). However, footplate-type haptics are attended by disadvantages, such as the addition of extra material weight to the IOL and reduced flexibility, as compared to filament haptics, leading to poor fixation and consequent migration or dislocation of the IOL.

Although the filament haptics are generally preferred over the footplate-type haptics for several reasons, certain difficulties remain. For example, filament haptics and soft or deformable optics tend to be formed from dissimilar materials which do not ordinarily chemically bond together. As a result, filament haptics have been designed having a variety of attachment end configurations or structures. For example, anchor structures that provide a physical or mechanical interlock between the haptic and optic are used. Polypropylene haptics, for example, have heretofore been secured into silicone polymer-based optics by means of a mechanical lock and other means that require complicated manufacturing steps to produce. These means include pouring a precursor material for the optic into a mold in which the haptic has already been placed, and then curing the optic around the proximal end of the haptic. Another means is to drill a hole into a pre-formed optic and then chemically or otherwise enhance the bond between the optic and the end of the filament haptic inserted into the drilled hole in the optic.

While procedures such as these can be effective for enhancing the haptic/optic bond strength, they may be relatively sophisticated and relatively expensive to practice. In addition, substantial care must be exercised in some of these manufacturing processes due to the extremely low tolerances of the materials to process and material variabilities. Moreover, even though these procedures can produce a bond between the haptic and optic sufficiently secure for purposes while the IOL is implanted within the eye, quite often the handling of the IOL prior to inserting it into the eye can subject the haptic to greater forces.

Therefore, it would be advantageous to provide a relatively straightforward and easy to practice method of producing IOLs which have substantial pull strength between the haptics and the optic. One easy way to accomplish this is to integrally form the optic and haptics in a single molding step, in which case, the haptics would be the same material as the optic. Because the optic is required to be made from a biologically inert and optically transparent material, such as polymeric silicone, haptics made from this material would not promote the fibrosis necessary to anchor the haptics to the surrounding tissue. This may lead to poor fixation and consequent migration or dislocation of the IOL.

SUMMARY OF THE INVENTION

The present invention is directed to new intraocular lenses (IOLs) and methods for making the same. These intraocular lenses include an optic and a haptic having a polyimide coating at least on the distal end of the haptic away from the optic. The polyimide coating is formed by applying a polyimide pre-cursor on at least the distal end of the haptic, and then curing the polyimide pre-cursor. Preferably, the intraocular lens is made from an integrally formed optic and haptic composed of silicone polymeric material. Being integrally formed, the haptic is structurally and integrally secured to the optic. Preferably, some form of adhesion promoter is applied to the haptic to enhance the bonding of the polyimide coating to the haptic. The IOLs of this invention are believed to have substantial haptic/optic bond strength so as to resist detachment of the haptic from the optic during normal surgical implantation and/or use.

In a broader aspect, this invention is directed to applying a polyimide coating to a portion of any device for implanting in human tissue where it is desired to enhance the anchoring of the device to the surrounding human tissue. Examples of such devices include pacemakers, venous grafts and stents.

In another aspect, the present invention is directed to a method for manufacturing an IOL. This method comprises integrally forming an optic and a haptic, then optionally exposing at least the distal region of the haptic to an adhesion promoting treatment. The adhesion promoting treatment may consist of exposure to a plasma, to an electrical corona discharge, or to a primer solution. The treated haptic is coated with a polyimide pre-cursor. This coating is then subject to a curing process to cure the polyimide and create strong bonding to the underlying haptic core. Preferably, the polyimide pre-cursor is photocurable, and the curing process is simply exposure of the IOL to actinic radiation, such as ultraviolet light. The advantages of this process and the IOLs made thereby are the secure attachment of the haptic to the optic, and the simplified manufacturing process. Since only the surface of the IOL haptic is needed to promote fibrosis of the surrounding eye tissue to secure the IOL in position, polyimide is provided only where needed to simplify manufacturing and reduce costs.

These and other aspects of the present invention are set forth in the following detailed description, examples and claims, particularly when considered in conjunction with the accompanying drawings.

DETAILED DESCRIPTION OF THE PREFERRED EMBODIMENTS OF THE INVENTION

In one aspect, the present invention is directed to novel intraocular lenses (IOLs) comprising an optic and fixation members. In the IOLs of this invention, the fixation member or members may be integrally attached or formed with the optic to achieve high pull strengths, and the distal end portion of the fixation members may be modified to achieve a surface that will suitably promote fibrosis in the eye, thereby anchoring the IOL to the surrounding physiological structure. Because the optic and fixation member are integrally formed, there is little or no risk of the fixation member being separated from the optic. By the phrase integrally formed, it is meant that the optic and haptic are monolithically formed, that is, cast as a single piece. And because the surface of the haptic can be treated to achieve suitable fibrosis promotion for anchoring, there is no concern about the biological inertness of the material that is used to form the core of the haptic and optic.

Fibrosis means the formation of fibrous tissue, also called scar tissue. Fibrosis is the bodies normal reaction to trauma and injury. For example, secondary to a laceration, the body heals the lacerated skin through the formation of fibroblasts in the injured area. The fibroblasts form connections between other fibroblasts and to the edges of the injured area until the lacerated area has been closed. The connection between fibroblasts and original tissue is fiber-like strands of protein that lay the foundation for fibrosis.

However, fibrosis can be prevented by the use of fibroid-preventing polymers. For example, the use of anionic polymers to prevent fibrosis is discussed by Roufa et al., U.S. Pat. No. 5,705,177. Roufa et al. discussed their desire to find a polymer that prevented the formation of scar tissue. Although many polymers provide a poor surface for the attachment of fibroblasts, and Roufa et al. discovered that some polymers, as previously stated, actually prevent fibroblast formation.

One embodiment of the present invention in contrast, is the use of a polymer coating on the haptics of an IOL to promote the formation and attachment of the haptic to nearby tissue through fibrosis. The polymer may be of any chemical composition and structure so long as it promotes fibrosis.

Intraocular lenses according to the present invention may have a variety of shapes. Generally, these IOLS include an optic, which has an optical zone through which light passes so that the wearer of the IOL has improved vision, and at least one fixation member, preferably two fixation members, having a distal end portion or anchoring region located away from the optic.

Figure 1:
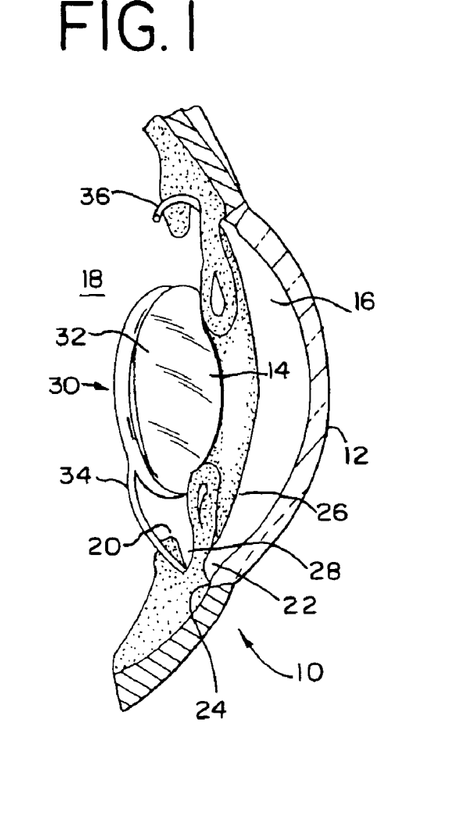
FIG. 1 is a cross-sectional representation of the human eye illustrating the placement of an intraocular lens (IOL).

Referring now to FIG. 1, there is depicted the in vivo placement into an eye 10 of an IOL 30 according to the present invention, in which anchoring regions of the filament-type haptics have been doubly coated with a primer coating and a polyimide coating. The cornea 12 serves as a refractory medium in addition to its function as the anterior wall of the eye 10. The pupil 14 and the iris 26 of variable aperture are located behind the cornea 12 and divide the eye into an anterior chamber 16 and a posterior chamber 18. The natural crystalline lens (not illustrated) is connected by zonular fibers to a peripheral muscle about the lens known as the ciliary muscle 20.

The surgical implantation of IOL 30 is accomplished by an incision in the eye, removal of the diseased or damaged natural lens (if applicable) and insertion of the IOL into the eye. The optic 32 of IOL 30 includes a centrally located optical zone and may be configured for implantation into one or either of the anterior or posterior chambers 16 or 18. The haptics 34 of IOL 30 extend radially outwardly in the general plane of the optic 32.

A peripheral limit of anterior chamber angle 22 exists between the base of the iris 26 and a scleral spur, which serves as a support location for IOL 30 implanted within the anterior chamber 16 of the eye 10. A peripheral zone 28 also exists within the posterior chamber 18 between the ciliary muscle 20 and the base of the iris 26, which is known as the ciliary sulcus 24. The peripheral zone 28 serves as a mounting location for IOL 30 within the posterior chamber 18. IOL 30 is shown positioned in the posterior chamber 18 and is supported by the haptics 34 bearing upon the ciliary sulcus 24.

Figure 2:
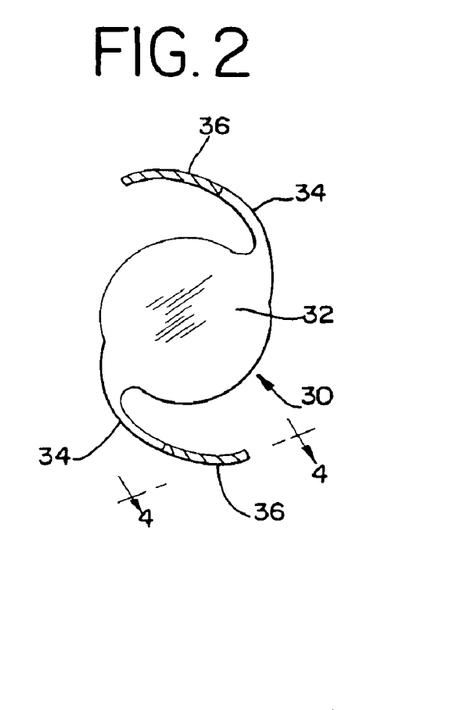
FIG. 2 is a plan view of an IOL in accordance with the present invention.
Figure 3:
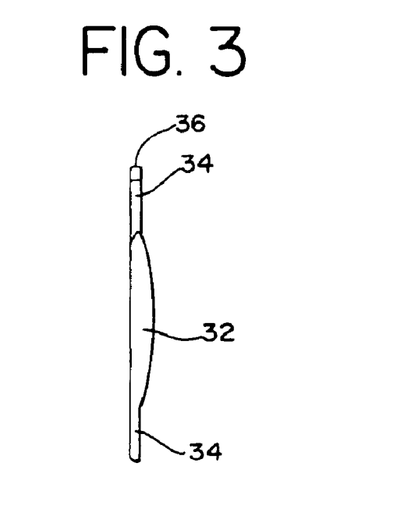
FIG. 3 is a side view of the IOL of FIG. 2.

Referring now to FIGS. 2 and 3, an IOL 30 is illustrated as including a pair of radially outwardly extending filament-type haptics 34 integral with optic 32. The optic 32 is made of an optically clear, silica reinforced, platinum-catalyzed, vinyl/hydride addition cured (cross-linked) polyorganosiloxane polymer and has an index of refraction (refractive index) of about 1.46. Each haptic 34 has a substantially uniform cross-sectional shape throughout its length and is shown provided with a polyimide-coated anchoring region 36, for contact with the peripheral zone of the ciliary 28. The coated anchoring region 36 generally has a greater cross-sectional area than the uncoated regions due to the extra thickness of the coating.

Figure 4:
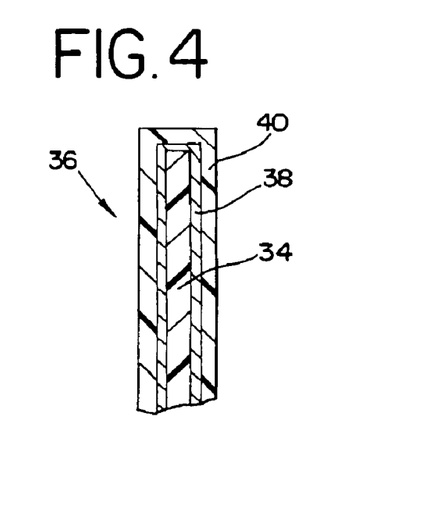
FIG. 4 is a cross-sectional view across lines 4—4 of the fixation member of FIG. 2.

FIG. 4 depicts the cross-sectional detail of the anchoring region 36 of the haptic 34 shown in FIG. 2. In this embodiment, the figure illustrates a doubly coated haptic 34 according to one embodiment of the present invention. The haptic core 34 is a silicone polymeric material integrally formed with the optic. Surrounding the haptic core 34 is a primer coating 38. Surrounding the primer coating 38 is a polyimide coating 40. Although FIG. 4 is not to scale, it can be appreciated that two coatings on the silicone haptic core 34 can substantially add to the thickness of the haptic. Depending on the material chosen for the primer components and polyimide coating and the coating thickness, these coatings may substantially stiffen the anchoring region 36. Preferably, the proximal portion of the haptic remains free of a coating to maintain the flexibility and springiness of the haptic.

Figure 5:
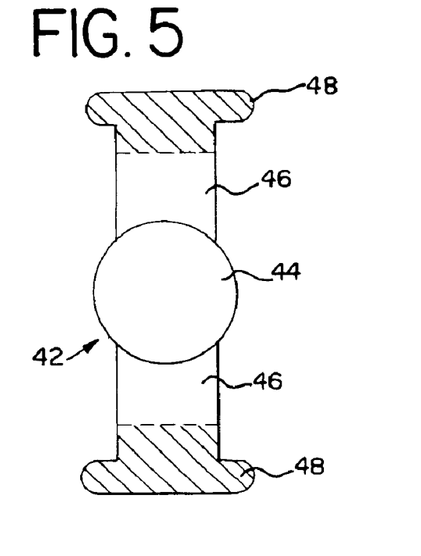
FIG. 5 is a plan view of an alternative embodiment of an IOL in accordance with the invention.

FIG. 5 depicts an intraocular lens having footplate-type fixation members or haptics. The optic 44 and two haptics 46 are integrally formed from a silicone polymeric material. The two haptics 46 are diametrically opposed and extend radially away from the optic 44. At the end of each haptic 46 is an anchoring region 48 that is coated with a polyimide material. The end of the anchoring region 48 has a greater width than the footplate 46 in order to provide a larger surface area to secure the intraocular lens into the ciliary sulcus. In this embodiment, the polyimide coating is applied to the end of the haptic that has been subjected to a corona electrical discharge to chemically activate the end of the haptic to enhance the bonding to the polyimide pre-cursor, coating. After the polyimide pre-cursor coating is applied to the haptic, the pre-cursor is subject to a curing step by applying UV radiation for a sufficient amount of time to convert the pre-cursor to polyimide and/or crosslink the polyimide material.

Figure 6:
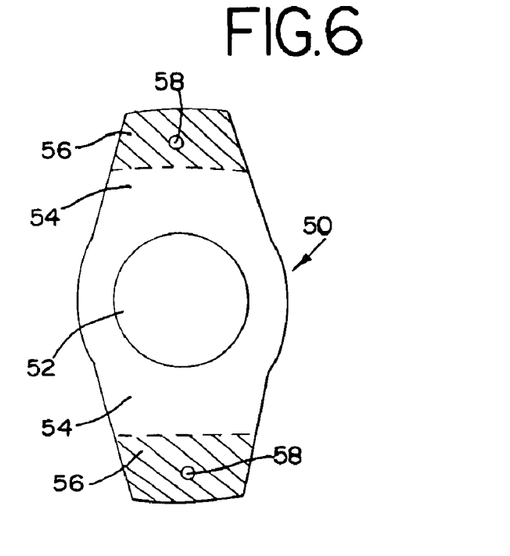
FIG. 6 is a plan view of another alternative embodiment of an IOL in accordance with the invention.

FIG. 6 depicts an alternative embodiment of an intraocular lens 50 having footplate-type haptics. The optic 52 is centered about a large planar member that surrounds the optic and has two footplate-type haptics 54 extending radially away from the optic 52. The ends of the haptics have a polyimide coating 56 adhered thereon. Also, there is provided a hole 58 in each end of the haptic that is useful for handling of the intraocular lens 50 prior to insertion in the eye.

Figure 7:
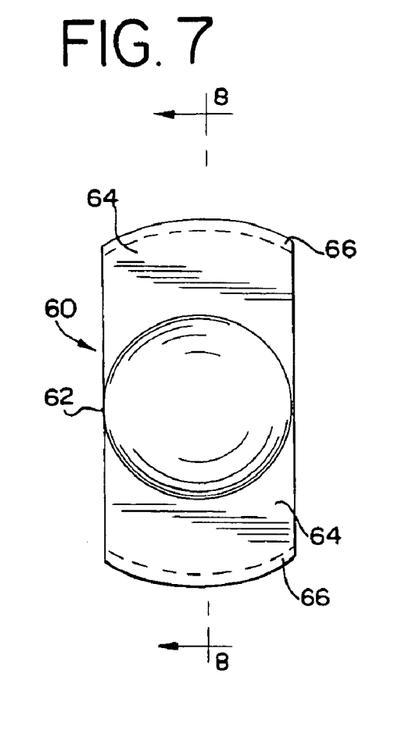
FIG. 7 is a plan view of yet another alternative embodiment of an IOL in accordance with the present invention.
Figure 8:
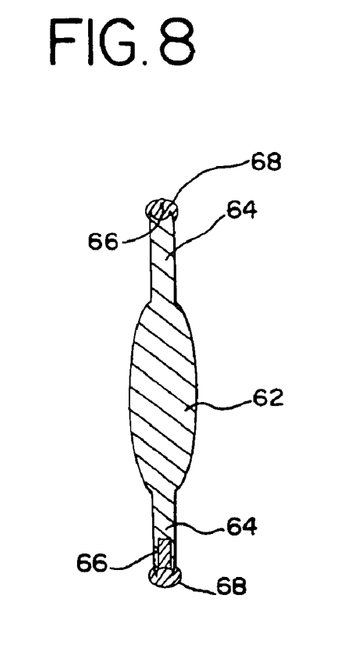
FIG. 8 is a cross-sectional view across lines 8—8 of the embodiment of FIG. 7.

FIGS. 7 and 8 illustrate another alternative embodiment of an intraocular lens 60 having footplate-type haptics. The optic 62 is centered between two plate-type haptics 67 that extend radially away from the optic. At the peripheral end of each haptic 64 there is a groove formed in the peripheral edge. The groove 66 extends across the full width of the haptic 64. As shown in FIG. 8, a polyimide coating is applied to the interior of groove 66. The polyimide material 68 fills the groove and extends outwardly away from the haptic 64. In this embodiment the polyimide coating is limited only to the peripheral edge of the intraocular lens.

Another aspect of the present invention relates to methods of making IOLs. These methods preferably include integrally forming an optic member and fixation members. Although other suitable techniques may be employed to form the IOL core, one particularly useful approach is to form a pre-cursor composition and inject such pre-cursor composition into a suitable mold. The pre-cursor-containing mold is then subjected to effective conditions, for example, conventional silicone curing conditions, to cure the pre-cursor composition into the desired silicone polymeric material. The cured material is then removed from the mold and is ready for additional processing in accordance with the present invention. Of course, pre-formed optic members can be provided from other sources and, therefore, the optic member forming need not be a part of the present methods.

One advantage of injection molding the IOL is that different but compatible formulations may be separately injected into the optic and haptic mold regions. In this way, the functional characteristics of these two parts of the IOL may be optimized. For example, even though both the optic and haptic are monolithically formed from a silicone polymeric material, the formulation injected into the haptic mold region need not include ultraviolet chromophores. Likewise, additional reinforcing components may be added to the haptic mold region to strengthen or add springiness to the haptic.

Each filament-type fixation member, or haptic, preferably comprises a flexible member made from a polymeric silicone material with a polyimide coating. The haptic has a substantially circular cross-section, although alternate cross-sectional configurations may be substituted, if desired. The cross-sectional area of the uncoated and coated regions of the fixation members is preferably substantially uniform along its length. The fixation members have sufficient strength to provide support for the IOL in the eye.

Each footplate-type fixation member, or haptic, typically comprises a less flexible plate comprising, preferably, polymeric silicone material with a polyimide coating on the distal end anchoring region. The footplate-type haptic can take a variety of shapes as known in the art. Compared to filament-type haptics, footplate-type haptics have greater rigidity to resist the forces of the capsular bag during healing. This type of haptic can resist vaulting and better maintain the optic in a centered position.

The optic and haptic core may be made from a variety of materials such as those that are typically used for making intraocular lenses. Those materials include, but are not limited to, silicone polymer, acrylic polymer, hydroacrylic polymer, 2-hydroxyethylmethacrylate polymer and polymethylmethacrylate polymer.

Preferably, the optic and haptic core of the IOL is made from a silicone polymeric material, for example, an elastomeric silicone polymeric material, which is preferably crosslinked. In brief, the IOL may be derived from a two part silicone formulation which is introduced into a mold cavity at a weight ratio of about 1:1, as is known to one of skill in the art. Part A typically includes a catalyst and a base polymer. Part B typically includes a cross-linker and the same base polymer. The base polymer is preferably synthesized from siloxanes.

In one particularly useful embodiment, the optic comprises a polymer that is a platinum-catalyzed, vinyl/hydride, addition cured poly-organosiloxane. One particularly useful composition includes a silicone polymeric material that is reinforced, for example, with an effective reinforcing amount of a suitable resin and/or silica. The composition may include one or more other components in amounts effective to provide a beneficial property to the optic. For example, an effective amount of an ultraviolet light absorbing component may be included, preferably covalently bonded to the silicone polymeric material of the optic. Benzophenones and benzotriazoles are just two classes among many ultraviolet absorbing compounds that may be used. Further details are described below.

Virtually any polymer can be used that allows for the formation of the exact optical specifications of the lens. In this regard, it is foreseen that any suitable monomer or block copolymer can be used in the practicing of this invention. By "suitable" it is meant that the formation of the polymer must be controllable so as to provide the desired refraction of light. Suitable monomers include, for example, PMMA, HEMA, vinyl pyrrolidone, acrylamid monomers and acrylic monomers either simply polymerized or combined and co-polymerized.

The present methods for producing IOLs include treating at least the distal end portion or lens anchoring region of the fixation member to promote the adhesion of a polyimide coating. One such method for treating includes coating the fixation member with a primer component at conditions effective to form a coated fixation member. This coated fixation member includes an effective coating of primer component located on the distal end portion of the fixation member. The primer component coating is effective to enhance the bond strength between the fixation member and a polyimide pre-cursor coating.

The primer component employed in the present invention may be any suitable primer material or combination of primer materials which function as described herein to produce a secure bonding between the silicon haptic and the polyimide coating. Many primer materials are conventional, well known in the art and commercially available. Without wishing to limit the present invention to any particular theory of operation, it is believed that the primer component interacts with or otherwise conditions the fixation member, for example, the surface of the distal end portion, to render it more compatible or susceptible to being bonded to polyimide.

In one useful embodiment, the primer component is selected from silanes or orthosilicates, metal-containing components and mixtures thereof. Examples of useful primer components include organo silanes or orthosilicates, such as silanes including alkoxy groups and/or substituted alkoxy groups each having 1 to about 6, preferably 1 to about 4, carbon atoms (or orthosilicates including alkyl groups or substituted alkyl groups each having 1 to about 6, preferably 1 to about 4, carbon atoms); organo titanium-containing components, such as titanates including alkyl groups or substituted alkyl groups each having 1 to about 6, preferably 1 to about 4, carbon atoms; and mixtures thereof. Such alkoxy groups include methoxy, ethoxy, propoxy, butoxy, pentoxy, hexoxy and the like. Such alkyl groups include methyl, ethyl, propyl, butyl, pentyl, hexyl and the like. As used herein the terms "substituted alkoxy group" and "substituted alkyl group" refer to the alkoxy group and the alkyl group, respectively, in which at least one of the H atoms has been replaced by another species, e.g., group, including one or more atoms of elements such as carbon, hydrogen, oxygen, silicon, nitrogen, sulfur, phosphorus and the like and mixtures thereof.

Specific useful primer components include products containing one or more of tetra(2-methoxyethoxy) silane, tetrapropylorthosilicate and tetrabutyltitanate, such as materials sold by NuSil Technology under the trademarks CF1-1357, CF2-135 and CF6-135, and the material sold by Dow Coming under the trademark Dow 1200. Mixtures of these materials are also useful.

The coated fixation member should have a sufficient amount of the primer component so as to yield an IOL having a secure bond between the silicone haptic and polyimide coating, as described herein. The primer component may be present in an amount in the range of about 0.1% or less to about 50% or more of the weight of that portion of the fixation member that is coated with the primer component.

In a particularly useful embodiment, the distal end portion of the fixation member is dipped in or otherwise contacted with a liquid medium containing the primer component, for example, for a time in the range of about 0.5 second to about 2 minutes, preferably about 0.5 second to about 30 seconds, so as to form a primer coating on the distal end portion of the fixation member. After this coating is formed, the coated fixation member is exposed to conditions to dry or otherwise remove the liquid medium from the coating, leaving a coating comprising the primer component on the distal end portion of the fixation member. Care should be taken in removing the liquid medium not to do so at conditions which would detrimentally affect the chemical makeup and/or functioning of the primer component. In most instances, the removal of the liquid medium can be accomplished at room temperatures or at temperatures below about 40° C. The coated fixation member is preferably maintained at conditions effective to remove the liquid medium for a period of time in the range of about 1 minute to about 60 minutes or more, more preferably in the range of about 2 minutes to about 20 minutes. Very useful results can be obtained when the proximal distal end portion of the fixation member is dipped in the liquid medium containing the primer component for about 1 second, and the coated fixation member is subjected to drying or liquid medium removal conditions for about 5 minutes.

The primer component is preferably soluble in the liquid medium employed. The liquid medium is preferably non-aqueous-based. Particularly useful results are obtained employing organic components, for example, hydrocarbon-based components, as the liquid medium or carrier for the primer components. Examples of useful organic components include naphtha, lower alkanols (such as propanol and butanol), glycols and mixtures thereof. The primer component may comprise about 1% or less to about 10% or more by weight of the primer component/liquid medium mixture.

The distal end portion of the primer-coated fixation member is dipped in or otherwise contacted with a precursor composition of a cross-linked photocurable polyimide precursor material so as to form a doubly coated fixation member. Thus, the distal end portion of the fixation member has an inner coating of primer component and an outer coating of the above-noted pre-cursor composition. The coating of pre-cursor composition is preferably present in an amount effective to react with residual reactable groups on the primer-coated surface of the fixation member core (for example, while the precursor composition is being cured). Thus, the cros-linked polymer produced from the pre-cursor composition forms a strong adhesive bond to the silicone polymeric material of the fixation member. The pre-cursor composition coating may be present in an amount in the range of about 10% or less to about 100% or more by weight of the length of the fixation member coated by the precursor composition. This pre-cursor composition may be chosen from those conventionally employed in producing cross-linked polyimide materials, for example, for use in IOLs. In general, the pre-cursor will be one or more monomers capable of polymerization and attachment to the haptic or device that also demonstrates fibrosis formation propensity after polymerization.

The polyimide pre-cursor composition is selected from compositions that are known to be photocurable, because thermally curable polyimide pre-cursor compositions generally require a high curing temperature that may degrade the silicone polymeric material of the IOL. Photocurable pre-cursors would not subject the IOL to a treatment that would degrade the silicone material, and also can be processed in a simpler manufacturing process. Additional methods of causing the polymerization of the pre-cursor are also foreseen such as e-beam, microwave, free radical induction, electro-chemistry and chemical induction.

With the coated fixation member in place, the optic member and coated fixation member are subjected to conditions effective to cure the pre-cursor composition of the cross-linked polymeric material located on the fixation member. Such conditions are substantially as conventionally used to cure such pre-cursor compositions and form cross-linked polyimide materials. However, the time during which such curing takes place is relatively limited because of the relatively limited amount of pre-cursor composition to be cured.

Further, the ability to coat the polyimide on an IOL provides manufacturing advantages. Also, the ability to apply the polyimide pre-cursor to the IOL at high solids content means that a thicker coat can be applied and the desired thickness can be achieved with fewer passes, ideally with one pass.

Still further, rather than a pre-cursor such as polyamic acid, the polymer may be applied as a polyimide. The polyimide coating is then exposed to actinic radiation in order to crosslink the polyimide within itself and to the primer coating with no further imidization required. Therefore, prior art problems associated with water formation during the imidization process may be avoided. In addition, a specific polyimide may be selected that is soluble in low boiling point solvents, for example, dichloromethane. Therefore, residual solvent removal is rapid and can be accomplished with a low temperature oven or under the low temperatures associated with UV exposure.

After this curing step, the resulting intraocular lens assembly may be subjected to additional procedures, for example, conventional lens finishing procedures to produce the final IOL.

An additional important advantage of the present invention is the predictability and reproducibility of the present methods. Thus, in order for a method of producing IOLs to be commercially effective, the method should produce IOLs which have reliably and predictably reproducible properties, for example, to avoid the production of undue amounts of waste materials and to improve cost effectiveness.

Without wishing to limit the invention to any particular theory of operation, it is believed that the predictability and reproducibility of the present methods are directly linked to the relatively straight forward and unsophisticated nature of the present methods. The compositions of the optic member, of the fixation member, of the primer component, and of the pre-cursor composition of a cross-linked silicone composition can be very reliably set and controlled. In effect, each of the steps of the present methods is relatively easy to effectively control resulting in an intraocular lens assembly which has reliable, predictable and reproducible properties.

Alternatively, a primer coating need not be applied to the fixation member prior to coating with a polyimide pre-cursor. It is envisioned that other methods of promoting adhesion between the silicone haptic and polyimide coating may be used. For example, other methods for treating surfaces to enhance their surface energy and reactivity are known.

Methods for increasing the surface energy of polymers include flame treatment, plasma and chemical etching and electrical surface treatment. The method preferred in one embodiment of the invention is electrical surface treatment, otherwise referred to as corona treatment. It has been found that monomers polymerized on a surface to which accelerated electrons have been directed bind to the treated surface. It is believed that this effect is caused indirectly by the electrons ionizing oxygen that then interacts with the polymer surface. Equipment employed for corona treatment has been commercially available for many years. An example of one model is the Electro-Technic Products High Frequency Corona Surface Treater Model BD-80, or other piece of equipment. The equipment to carry out this method includes a set of electrodes that conform to the area where treatment is desired, a high voltage transformer and a high frequency generator with impedance matching electronics. The operating frequency may be adjusted based on impedance up to 25 kHz with a typical frequency from 50 to 500 Hz operating at a voltage between 2 kV and 80 kV, typically from 14 to 50 kV, for example. With this combination of high frequency and high voltage, it is possible to maintain a distance of about 1½ inches and a relatively short treatment time, typically a corona discharge period between 0.2 and 2.0 seconds, by making the plasma between the electrodes fairly intense. In performing the surface treatment, the electrodes may be placed between 0.25 mm and 0.5 mm from the surface of the piece to be treated.

While the exact mechanism causing the polyimide or pre-cursor material to adhere to the corona treated fixation member is not known, electrical surface treatment effectiveness has been linked by theory to such phenomenon as ablation (surface degradation), cross linking of the polymer, oxidation, hydrogen bonding and electret formation. While the mechanism is unclear, it is believed that one of the parameters effecting the strength of adhesion between the polyimide pre-cursor and the fixation member may be the amount of oxygen present before and during treatment of the fixation member surface. Generally, the lower the oxygen level, the lower the bound oxygen to the surface, and the less adhesion between the polyimide pre-cursor and the fixation member. For this reason, it is best that oxygen contact with the polyimide pre-cursor and the fixation member be minimized prior to treatment. Other parameters effecting the adhesion strength are power of the electrodes and time of treatment as well as treatment frequency and voltage.

Chemical etching is another method for treating the surface of the fixation member. For example, the use of oxidizing agents is useful for etching the surface before treatment with the liquid containing the polyimide monomers. Trifluoro acetic acid may be used for pretreatment by application for 1 second to 20 minutes, preferably less than 5 minutes. The trifluoro acetic acid is preferably used neat, although it may be diluted with a non-reactive solvent. Chromic acid, which may be in an acetone solution, may also be used for pretreatment. The chromic acid should be in the concentration range of 0.01 to 0.5 molar, preferably 0.1 molar, for a time period ranging from 10 seconds to 20 minutes, preferably less than 5 minutes. In addition, nitric acid, in the concentration of 0.1 to 1.0 molar in a water solvent, preferably 5 molar in a water solvent, for 10 seconds to 20 minutes, preferably less than 5 minutes, may be used as a pretreatment.

As noted above, silicone polymeric materials may be used as materials of construction for the optic and fixation core members. Particularly useful materials are reinforced elastomeric compositions including polysiloxane elastomers, preferably having the chemical composition of a cross-linked copolymer including about 12 to about 18 mol percent of aryl substituted siloxane units of the formula $R_4R_5$—SiO where the aryl substituents ($R_4$ and $R_5$ groups) can be independently selected from phenyl groups, mono-lower alkyl substituted phenyl groups, and di-lower alkyl substituted phenyl groups. Preferably, both aryl groups are simple phenyl, and the resulting diphenyl siloxane unit is present in the copolymer in an amount of about 14 to about 18 mole percent.

The copolymer is end blocked with trisubstituted (monofunctional)siloxane units. At least one substituent of the end blocking group contains an olefinic bond. Thus, the general formula of the end blocking group incorporated in the copolymer is $R_1R_2R_3SiO_{0.5}$ where the nature of the $R_1$ and $R_2$ is not critical, and they may be independently selected from, for example, alkyl, aryl, substituted alkyl and substituted aryl groups. $R_3$ contains an olefinic bond. $R_3$ is preferably an alkenyl group, more preferably a vinyl group. In a preferred embodiment, the end blocking group is a dimethyl, vinyl siloxane unit. The role of the olefinic (vinyl) group is to enable curing or cross-linking of the polymer, and preferably covalently linking certain ultraviolet light absorbing compounds to the cross-linked copolymer matrix.

The balance of the siloxane building blocks of the copolymer is preferably dialkyl siloxane units wherein the two alkyl substituents are either ethyl or methyl. In other words, the general formula of the balance of the siloxane building blocks of the copolymer is preferably $R_6R_7$—SiO where the $R_6$ and $R_7$ groups are independently selected from methyl and ethyl. Preferably both $R_6$ and $R_7$ groups are methyl. The copolymer may have a degree of polymerization (dp) of about 100 to about 2000, although a degree of polymerization of about 250 is preferred, particularly when the $R_4$ and $R_5$ groups are phenyl and the $R_6$ and $R_7$ groups are methyl.

The preparation of the copolymer having the above described components can be performed in accordance with processes known in the art, and from starting materials that are either commercially available or that can be made in accordance with well known processes.

The elastomeric silicone composition preferably contains a reinforcer, for example, a fumed silica reinforcer, such as trimethylsilyl treated silica reinforcer, finely dispersed therein. The reinforcer, for example, the fumed silica reinforcer, is preferably used in an amount of about 15 to about 45 parts by weight of the reinforcer to 100 parts of the copolymer. Fumed silica itself is commercially available. The fumed silica reinforcer preferably used has a surface area of about 100 to about 450 meter$^2$/gram. More preferably, the fumed silica has a surface area of about 200 meter$^2$/gram, is present in an amount (by weight) of about 27 parts (by weight) to 100 parts (by weight) of the copolymer, and is trimethylsilylated with hexamethyldisilazane substantially in the same step where the copolymer is intimately mixed with the silica.

The intimate mixture of the fumed silica with the copolymer is commonly termed the "base" in the art. For the purpose of making materials suitable for intraocular lens, the base may be dispersed in a suitable inert solvent, such as trichloro-trifluoroethane, and the dispersion filtered to remove any solid impurities. Thereafter, the solvent is removed by gentle heat and vacuum.

In accordance with standard practice in the art, the base is divided into two aliquots which preferably are of equal weight. The aliquots are commonly termed "Part A" and "Part B".

Silicon bonded hydride groups are added to the second aliquot (Part B) in the form of cross-linking agents, which are conventional and well known in the art. The liquid organohydrogen polysiloxane cross linkers having the formula $(R)_a(H)_b SiO_{4-ab/2}$ wherein R is simple lower alkyl, for example, methyl, and a ranges from about 1.00 to about 2.10 and b ranges from about 0.1 to about 1.0, are eminently suitable.

The platinum catalyst can be selected from materials which are conventional and well known in the art.

The cross-linking should not proceed too rapidly at room temperature, thereby allowing, at least two, preferably about six hours for work time with the mixed aliquots. For this reason, a suitable cross-linking inhibitor, such as 1,2,3,4-tetramethyl-1,2,3,4-tetravinyl cyclotetrasiloxane, may be added to the second aliquot (Part B).

Formation of the IOL may be accomplished by liquid injection molding, by cast, or by compression molding of the intimately mixed Parts A and B. The fixation member can be dipped in and/or otherwise contacted with photocurable polyimide pre-cursor, to form the coated fixation member useful in producing the present IOLs.

As used herein, photocurable means that the polyimide pre-cursor of the present invention is photosensitive and will polymerize, and if desired crosslink, upon being subjected to actinic radiation, such as UV radiation. Although it is not necessary to crosslink the haptic polymeric coating, crosslinking functions to harden the polymer coating, provide enhanced mechanical properties and improved solvent resistance, and/or enhance the bonding to the fixation member.

Examples of dianhydrides that will contribute a photosensitizing moiety include, but are not limited to 3,3',4,4'-benzophenone tetracarboxylic acid dianhydride (BTDA), 2,3,6,7-anthraquinone tetracarboxylic acid dianhydride, and the like, as well as isomers thereof Examples of diamines include, but are not limited to, the various isomers of benzophenone diamine, anthraquinone diamine, thioxanthone diamine, and the like.

Generally, polyimides are made by mixing a diamine component and a dianhydride component and adding a compatible solvent to form a solution of polyamic acid. The polyamic acid is then imidized by either chemical or thermal methods to form a polyimide.

A solid polyimide can be isolated from solution by precipitating the polyimide solution in low-polarity solvents, such as for example, alkanes such as pentane, hexane and heptane; alcohols such as methanol, ethanol and propanol; ethers such as diethyl ether, and the like. Preferably, the polyimide is precipitated with methanol, washed with solvent, and dried in air or inert atmosphere (such as nitrogen).

The solid polyimide then can be dissolved in a suitable solution solvent to form a coating composition. This composition is used to apply the polyimide coating to the haptic. Generally, the polyimide solution will be diluted with a low boiling point inflammable solvent, such as, for example, dichloromethane, or with halogenated hydrocarbons. The degree of dilution is based on the thickness requirement of the final coating and the desired viscosity and solids content of the solution. Typically, solutions of the polyimide are applied to the haptic with solids concentrations from about 5 to about 60 weight percent and preferably from about 5 to about 30 weight percent. Clean, dry, high-purity solvent (solution solvent) is generally used as the diluent. The diluted solution can be pressure-filtered before further processing.

The polyimide used in the present invention is preferably photosensitive and the coated IOL can be exposed to actinic radiation to effect crosslinking of the polymer. This photocrosslinking is brought about by actinic, or high-energy radiation, for example, by light within the region of 600 to 200 nm or the deep ultraviolet region, or by X-rays, laser light, electron beams, and the like.

A preferred polyimide is a polyimide having from about 30 to about 90 mole percent photosensitizing moiety derived from BTDA relative to the diamine moiety. As used herein, photosensitizing moiety means a moiety that increases the sensitivity of the polyimide to crosslinking as a result of exposure to actinic radiation. Because of the reduction in solution Brookfield viscosity, a more preferred concentration is from about 50 to about 90 mole percent BTDA.

In one embodiment of the present invention, when the polymer pre-cursor is first prepared, it is essentially in the polyamic acid form. However, the polymer is in a dynamic state and some polyimide may be present. Likewise, after the polyamic acid is cured to the polyimide form, some polyamic acid may be present. Accordingly, it is to be understood that although the coating of the present invention is a polyimide, it may contain some degree of polyamic acid.

A co-initiator may be included in the photocurable polyimide coating composition to further increase the photosensitivity of the polymer. These co-initiators may or may not be included in the polymer backbone. Examples include, but are not limited to, anthraquinone 2-ethylanthraquinone, 2-tert-butylanthraquinone, benzophenone, Michleer's ketone, thioxanthone, 3-ketocoumarines, triethylamine, N-methyl diethanolamine, 4-(amino) methyl benzoate, 4-(dimethylamino)methylbenzoate, 4-(dimethylamino) benzaldehyde, and the like.

One skilled in the art may appreciate that the methods and teachings contained herein can be applied to enhancing the securement of prosthetics and other devices surgically implanted into human tissue. For example, following the methods according to the present invention, one may take a pacemaker and treat the external housing of the pacemaker to enhance the bonding of a polyimide pre-cursor material to it. Subsequently curing the polyimide pre-cursor material will provide a secure polyimide coating to the pacemaker. The polyimide coating will help promote fibrosis of the human tissue next to which the pacemaker is implanted in a patient. Promoting fibrosis around the pacemaker will help to secure the pacemaker in a fixed position where it has been surgically implanted and minimize any movement and rotation of the device in vivo.

Likewise, the exterior surface of a venous graft may be suitably treated and a polyimide coating applied thereon. With a polyimide coating on the graft, the graft can be anchored more securely in a human by the enhanced fibrosis growth around the graft. Therefore, the graft can be more secure in place and less prompt to being torn out of position when the patient is subject to some form of extreme trauma such as an automobile accident.

The method of this invention has additional uses in the area of stents, corneal rings and implantable contact lenses, to name a few. The stents may be made from a variety of materials. Those materials include, but are not limited to, polyethylene, polyethylene interpolymers, polyethylene block copolymers, polypropylene, polypropylene interpolymers, polypropylene block copolymers, polyacrylonitrile, polyethylene terephthalate, or polybutylene terephthalate. The surface of the stent may preferably be treated to enhance the bonding of the polyimide coating which may be applied as heretofore described for other devices. Even without pretreatment of the stent surface, it may be possible for the polyimide coating to suitably adhere to the surface by encapsulating protruding portions or invading surface pores of the stent to which it may physically adhere.

EXAMPLES

For the purposes of illustration, the following examples enable one of skill in the art to practice the invention.

Example 1

The monomer or polyimide pre-cursor is prepared from 95 parts N-vinyl phthalimide (structure I), 4 parts EDMA as crosslinker and 1 part AIBN as photo-initiator and sufficient DMF (dimethylformamide) as solvent to effect solvation at 40° C. in a sonicator. The device to be coated (haptics) is coated with this liquid, either through dipping into the solution, or through other equivalent means. The resultant coated assemblage is then irradiated with UV-A light of 3.8 mW/cm$^2$ intensity for 1 hour, then is heated at 85° C. for 45 minutes. The coated object (lens) is placed in a saline bath for 2 hrs and then is sterilized according to means known in the art.

Example 2

The haptic is first activated through coronal treatment. Subsequent to coronal treatment, the haptic is coated with the monomeric mixture of Example 1 and polymerized according to the method of Example 1.

Example 3

The haptic of example 2 is subjected to microwave polymerization instead of photo-polymerization.

Example 4

The haptic is first activated, then is coated with monomer of structure II below, and then is photo-polymerized.

Example 5

The haptic is pretreated with a chemical oxidizing agent.

Example 6

The haptic is pretreated with substantially pure trifluoro acetic for 10 seconds to 2 minutes.

Examples of some monomers useful in the practice of this invention are depicted as structures I through VI below.

I

II

III

IV

One of ordinary skill in the art can envision additional amine monomers suitable for polymerization-adherance to the haptics according to this invention. Although the examples are directed to UV light and microwave energy induced polymerization, it should be understood that any means whereby a fibrosis-facilitating polymer is applied to all or a portion of a haptic or other device is within the scope of this invention.

Of course, it should be understood that changes and modifications can be made to the preferred embodiments described above. It is therefore intended that the foregoing detailed description be regarded as illustrative rather than limiting, and that it be understood that it is the following claims including all equivalents, which are intended to define the scope of this invention.

We claim:

1. An intraocular lens for surgical implantation in the eye, the lens comprising:
a unitary structure comprising a substantially homogeneous biologically inert transparent material wherein the unitary structure includes an optic portion and a haptic portion, with both the optic and haptic portions comprising a single casting of the same biologically inert transparent material, and wherein at least a distal portion of the haptic portion comprises a coating of a fibrosis-promoting amount of polyimide on the substantially homogeneous biologically inert transparent material.

2. The intraocular lens of claim 1 wherein the coating of a fibrosis-promoting amount of polyimide is formed by applying a photocurable polyimide pre-cursor and then curing the polyimide pre-cursor.

3. The intraocular lens of claim 1 wherein the optic and haptic portions comprise silicone polymer.

4. The intraocular lens of claim 1 wherein the optic and haptic portions comprise acrylic polymer.

5. The intraocular lens of claim 1 wherein the optic and haptic portions comprise 2-hydroxyethylmethacrylate polymer.

6. The intraocular lens of claim 1 wherein the optic and haptic portions comprise polymethylmethacrylate.

7. The intraocular lens of claim 1 wherein the optic portion further comprises a UV absorbing compound.

8. The intraocular lens of claim 1 wherein the surface of the haptic portion includes a surface active region wherein the surface active region increases the bonding strength between the haptic portion and the polyimide coating.

9. The intraocular lens of claim 8 wherein the surface activation of the haptic portion is by treatment by a corona discharge.

10. The intraocular lens of claim 8 wherein the surface activation of the haptic portion is by treatment by an oxidizing agent.

11. The intraocular lens of claim 1 wherein the surface of the haptic portion further comprises an adhesion promoter coating between the haptic surface and polyimide coating in an amount effective to enhance the bond strength of the polyimide coating to the haptic portion.

12. The intraocular lens of claim 11 wherein the adhesion promoter coating comprises a primer component.

13. The intraocular lens of claim 1 wherein the haptic portion is a filament.

14. The intraocular lens of claim 1 wherein the haptic portion is a footplate.

15. A unitary intraocular lens comprising:
an optic;
two plate haptics diametrically opposed and extending radially away from the optic, each of the haptics having a groove adjacent a distal peripheral edge; and
a fibrosis-promoting amount of a polyimide coating on the interior of the groove;
wherein the optic and the plate haptics comprise a unitary molding of the same substantially homogeneous biologically inert transparent material.

16. The intraocular lens of claim 15 wherein the optic further comprises a UV absorbing compound.

17. The intraocular lens of claim 15 wherein the optic and haptic comprise silicone polymer.

18. The intraocular lens of claim 15 wherein the optic and haptic comprise acrylic polymer.

19. The intraocular lens of claim 15 wherein the optic and haptic comprise 2-hydroxyethylmethacrylate polymer.

20. The intraocular lens of claim 15 wherein the optic and haptic comprise polymethylmethacrylate.

21. A device for implantation in a human to be anchored in a secured position within human tissue, the device comprising:
a biologically inert exterior surface region; and
fibrosis-promoting amount of a polyimide coating on at least an anchoring region of said surface region;
wherein the device is shaped in the form of an intraocular lens, the intraocular lens comprising an optic and at least one haptic which form a unitary structure with the anchoring region located away from the optic; and
wherein the optic and haptic, being a unitary molding formed of a substantially homogenous transparent composition, comprise a silicone polymer, an acrylic polymer, a hydroacrylic polymer, a 2-hydroxyethylmethacrylate polymer, a polymethylmethacrylate polymer, or a combination thereof.

22. The device of claim 21 wherein the haptic is shaped in the form of a filament.

23. The device of claim 21 comprising two haptics shaped in the form of a plate, diametrically opposed and extending radially away from the optic, each of the haptics having a groove in a distal peripheral edge, wherein the fibrosis-promoting amount of polyimide coating is on the interior of the groove.

24. The device of claim 21 wherein the polyimide coating is formed by applying a photocurable polyimide pre-cursor on at least the anchoring region of the haptic, and then curing the polyimide pre-cursor.

25. The device of claim 24 wherein the polyimide pre-cursor is photocurable by exposure to actinic radiation.

26. The device of claim 21 wherein the haptic includes a surface active region at least on the anchoring region wherein the surface active region increases the bonding strength between the haptic and the polyimide coating.

27. The device of claim 26 wherein the surface activation of the haptic at least on the anchoring region is by treatment by corona discharge.

28. The device of claim 26 wherein the surface activation of the haptic at least on the anchoring region is by treatment by an oxidizing agent.

29. The device of claim 21 wherein the haptic at least on the anchoring region further comprises an adhesion promoter coating between the haptic and polyimide coating in an amount effective to enhance the bond strength of the polyimide coating to the haptic.

30. The device of claim 29 wherein the adhesion promoter coating comprises a primer component.

31. The device of claim 21 wherein the polyimide coating is formed by treating at least the anchoring region of the surface of the haptic, applying a photocurable polyimide pre-cursor to the treated region, and curing the polyimide pre-cursor.

32. The device of claim 31 wherein the treating comprises exposing the region to a primer component, a corona electrical discharge, a gas plasma or a chemical etching.

33. The device of claim 31 wherein the polyimide pre-cursor is photocurable by exposure to actinic radiation.

34. The intraocular lens of claim 1 wherein the unitary structure is comprised of a hydroacrylic polymer.

35. The intraocular lens of claim 15 wherein the unitary structure is comprised of a hydroacrylic polymer.

36. The lens of claim 1 wherein only the distal portion of the haptic comprises the coating of a fibrosis-promoting amount of polyimide.

* * * * *